United States Patent [19]
Welch et al.

[11] Patent Number: 5,792,178
[45] Date of Patent: Aug. 11, 1998

[54] HANDLE LATCHING MECHANISM WITH RELEASE TRIGGER

[75] Inventors: Robert F. Welch, Maineville; John P. Measamer, Cincinnati, both of Ohio

[73] Assignee: Ethicon Endo Surgery, Inc., Cincinnati, Ohio

[21] Appl. No.: 661,681

[22] Filed: Jun. 11, 1996

[51] Int. Cl.⁶ .................................................. A61B 17/00
[52] U.S. Cl. .................................................. 606/208; 606/206
[58] Field of Search .................................. 606/208, 206, 606/207, 147, 148, 151

[56] References Cited

U.S. PATENT DOCUMENTS 1,659,112  2/1928  Littlejohn .
5,250,056  10/1993  Hasson ........................... 606/208
5,314,424  5/1994  Nicholas ......................... 606/41
5,498,256  3/1996  Furnish .......................... 606/208
5,591,176  1/1997  Henderson et al. ............. 606/208

*Primary Examiner*—Michael Buiz
*Assistant Examiner*—Kevin Truong
*Attorney, Agent, or Firm*—Bernard Shay

[57] ABSTRACT

A surgical instrument including an improved handle and latching mechanism is described. The handle comprises an instrument trigger pivotally connected to an instrument body with a toggle link connecting the instrument trigger to an actuating mechanism in the handle. The toggle link includes a latch notch or latch stop which is adapted to receive a latch link which is pivotally connected to the handle at a first end and contacts the toggle link at a second end. A latch trigger is adapted to contact the latch link.

9 Claims, 9 Drawing Sheets

HANDLE LATCHING MECHANISM WITH RELEASE TRIGGER

FIELD OF THE INVENTION

The present invention relates, in general, to a latch mechanism for a surgical instrument and, more particularly, to an improved latch mechanism including a positive release feature.

BACKGROUND OF THE INVENTION

In laparoscopic and other minimally invasive surgery, long shafted instruments are used through trocars to grasp, cut, dissect, and manipulate tissue. Instruments for use in laparoscopic, endoscopic and minimally invasive surgery generally have a handle external to the body cavity for controlling an end effector within the body cavity and an elongated shaft including a mechanism for transferring motion and force to the end effector. In such instruments, the end effector is generally a tool on the distal end of the coaxial shaft for cutting, grasping, or dissecting tissue. In addition, the coaxial shaft is generally rotatable with respect to the handle. Some such instruments may be provided with attachments for mono-polar and bi-polar energy. Electrosurgical instruments will generally have electrical insulation covering the coaxial shafts to protect the surgeon and patient.

In surgical instruments, proper ergonomics, control, and tactile feedback are important for the surgeon to properly perform the surgical procedure. Rough movement or sticky mechanisms complicate the procedure. For some applications a "clamp" is required for the purpose of holding retraction, providing fixed position manipulation, or rigidly holding ancillary equipment such as a suture needle. This clamping is traditionally accomplished, on open surgical instruments with scissors style handles, with a toothed "rack" on one actuator arm, and a mating "pawl" on the other actuating arm. The latching takes place along the medial plane of the instrument as described in U.S. Pat. No. 1,659,112 to Littlejohn. This method is effective for traditional surgical instruments, but it may be cumbersome on certain instruments designed for minimally invasive procedures including endoscopic instruments. Alternate clamping methods used in endoscopic instruments include: a rack and pawl, wherein the pawl is disengaged from the rack by depressing a release trigger; a "squeeze to lock" mechanism wherein the handle locks at the closed position, and is released by depressing a release trigger, similar to the method above; a "squeeze to lock, squeeze to open" mechanism wherein the handle locks at the closed position, and releases when squeezed again; and, a variation of the "squeeze to lock, squeeze to open" mechanism is where the trigger handle locks at an intermediate position, and releases at the full closed position.

While all of these mechanisms have proven effective, in certain circumstances and using certain handle designs, squeeze to release designs may not be desirable because it may be possible for the surgeon to accidentally release the clamping lock. For example, when the surgeons attention is focused on a task such as manipulating tissue, the surgeon may have a tendency to grip the instrument handle tighter, thereby effecting clamping release.

It would, therefore, be advantageous to design a squeeze to lock mechanism which is not squeeze to release, thus alleviating the problem described previously. It would further be advantageous to provide an improved latch wherein clamping release is effected by a two step process, firstly squeezing the handle trigger, and secondly squeezing the release trigger to effect clamping release. This two step process minimizes the chance of accidental release. It would further be advantageous to design a squeeze to lock mechanism wherein the instrument may be clamped in one of a plurality of positions.

SUMMARY OF THE INVENTION

The present invention is directed to a surgical instrument including an improved handle and latching mechanism. In one embodiment of the present invention, the handle comprises an instrument trigger pivotally connected to an instrument body with a toggle link connecting the instrument trigger to an actuating mechanism in the handle. In this embodiment, the toggle link includes a latch notch or latch stop which is adapted to receive a latch link which is pivotally connected to the handle at a first end and contacts the toggle link at a second end. A latch trigger is adapted to contact the latch link.

In a further embodiment of the present invention, the toggle link Is pivotally connected to the instrument trigger at a first end of the toggle link, the latch link includes a spring mechanism to force the second end of the latch link against the latch notch or latch stop against the latch link and the latch trigger contacts the latch link such that motion of the latch trigger acts against the spring mechanism. In a further embodiment of the present invention, the latch notch or latch stop is located between the first end of the toggle link and the actuating mechanism and the latch trigger is pivotally connected to the instrument trigger. In a further embodiment of the present invention, the toggle link includes a plurality of latch notches or latch stops.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
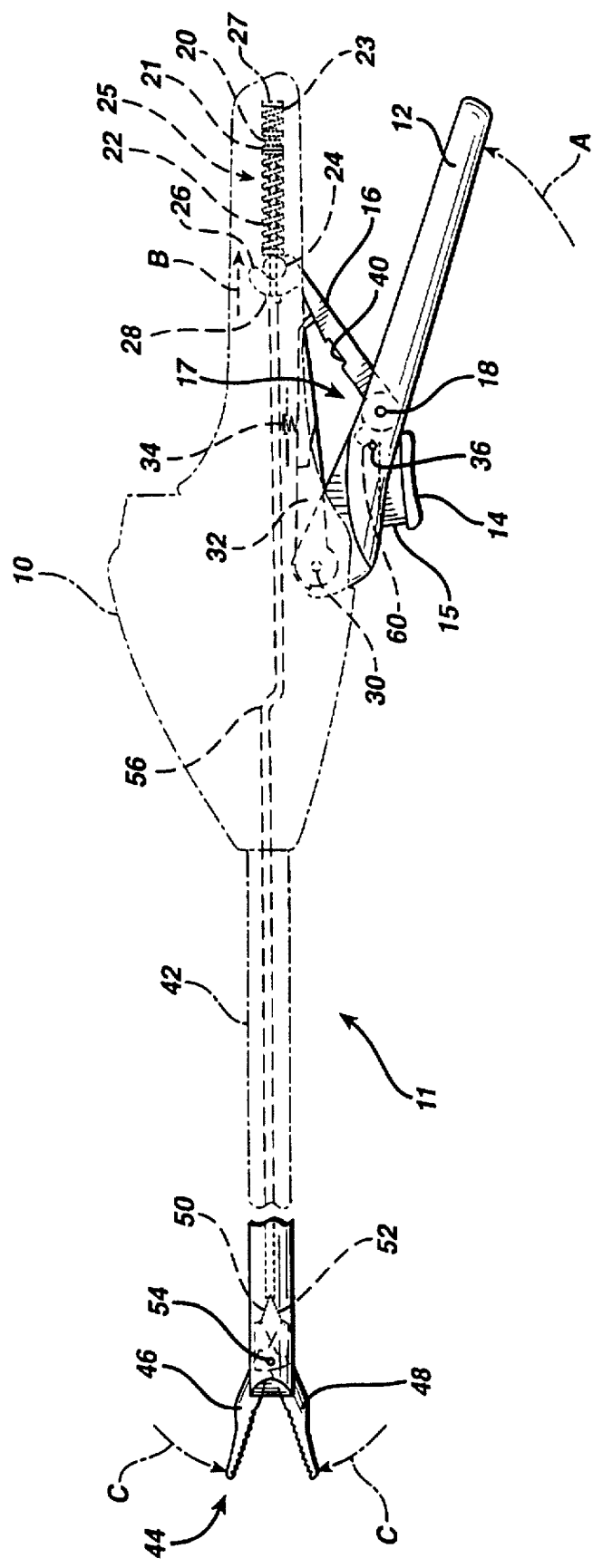
FIG. 1 is a side elevational view of a surgical instrument incorporating the handle latching mechanism with release trigger according to the present invention.

FIG. 1 is a side elevational view of a surgical instrument incorporating the handle latching mechanism with release trigger according to the present invention. In FIG. 1, surgical instrument 11 includes instrument body 10, elongated instrument shaft 42 and end effector 44. End effector 44 is connected to instrument body 10 by instrument shaft 42. Instrument body 10 includes instrument trigger 12, latching mechanism 17 and actuation mechanism 25. In the embodiment of the invention illustrated in FIG. 1, latching mechanism 17 connects instrument trigger 12 to actuation mechanism 25.

Latching mechanism 17 includes release trigger 15, toggle link 16, latch link 32, and bias spring 34. Release trigger 15, which includes release button 14, is connected to instrument trigger 12 by pivot pin 18 and rests against release trigger stop 36. Toggle link 16 is connected to instrument trigger 12 by pivot pin 18 and to actuation mechanism 25 by toggle link yoke 26. Toggle link 16 includes latch notch 40 which is positioned intermediate of pivot pin 18 and toggle link yoke 26. Latch notch 40 may comprise a notch or other type of latch stop, including a raised shoulder or raised post on toggle link 16. Latch link 32 is pivotally connected to instrument body 10 by pivot pin 30. Bias spring 34 acts to force the end of latch link 32 opposite pivot pin 30 against toggle link 16.

Actuation mechanism 25 includes adjustment nut 20, adjustment washer 21, compression spring 22, return spring 23, yoke pin 24, actuation rod stop 28 internal wall 27 and actuator rod 56. Actuator rod 56 connects instrument trigger 12 to end effector 44 through toggle link 16. Actuation rod stop 28 is fixed to actuation rod 56. Yoke pin 24 is slideably attached to actuation rod 56 and is held in place by toggle link yoke 26 and compression spring 22. Compression spring 22 is held in place by adjustment washer 21 and adjustment nut 20 which is fixed to threaded end 58 (see FIG. 2) of actuation rod 56. Return spring 23 is positioned between adjustment washer 21 and internal wall 27 of instrument body 10.

End effector 44 includes linkage 50, linkage 52, pivot pin 54, jaw 46 and jaw 48. Linkage 52 connects jaw 46 to actuation rod 56. Linkage 50 connects jaw 48 to actuation rod 56. Linkages 52 and 50 translate the linear motion of actuation rod 56 into a pivotal motion around pin 54 of jaws 46 and 48 respectively. Jaws 46 and 48 pivot around pivot pin 54 to open and close as actuation rod 56 moves distally and proximally. Thus, movement of instrument trigger 12 in direction A forces actuation rod 56 to move in direction B, closing jaws 46 and 48 of end effector 44 along path C.

Figure 2:
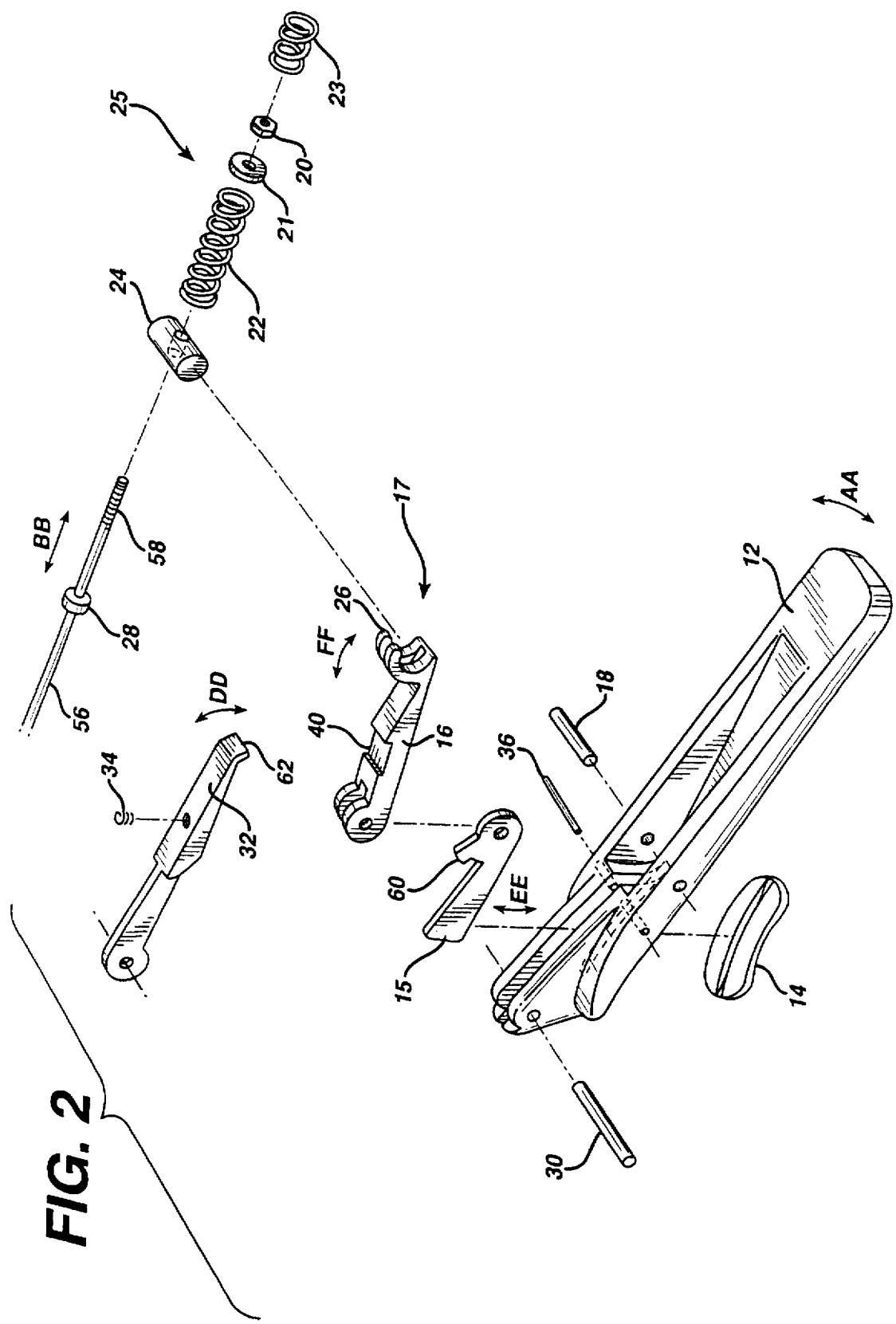
FIG. 2 is an exploded perspective view of the handle latching mechanism with release trigger according to the present invention.

FIG. 2 is an exploded perspective view of the handle latching mechanism with release trigger according to the present invention. As illustrated in FIG. 2, instrument trigger 12 moves in direction AA by pivoting around pivot pin 30. Movement of instrument trigger 12 is translated to toggle link 16 by pivot pin 18, forcing toggle link 16 to translate in direction FF and toggle yoke 26 to move actuation rod 56 in direction BB. Movement of toggle link 16 is translated to actuation rod 56 by actuating mechanism 25, forcing actuation rod 56 to move in direction BB. Release trigger 15 moves in direction EE by pivoting around pivot pin 18. When release trigger 15 is adjacent to latch link 32 as, for example, when instrument trigger 12 is locked in the closed position, movement of release trigger 15 in direction EE is translated to latch link 32 through release tab 60, forcing latch tab 62 of latch link 32 to move in direction DD. Movement of release trigger 15 in direction EE is limited by stop pin 36.

Figure 3:
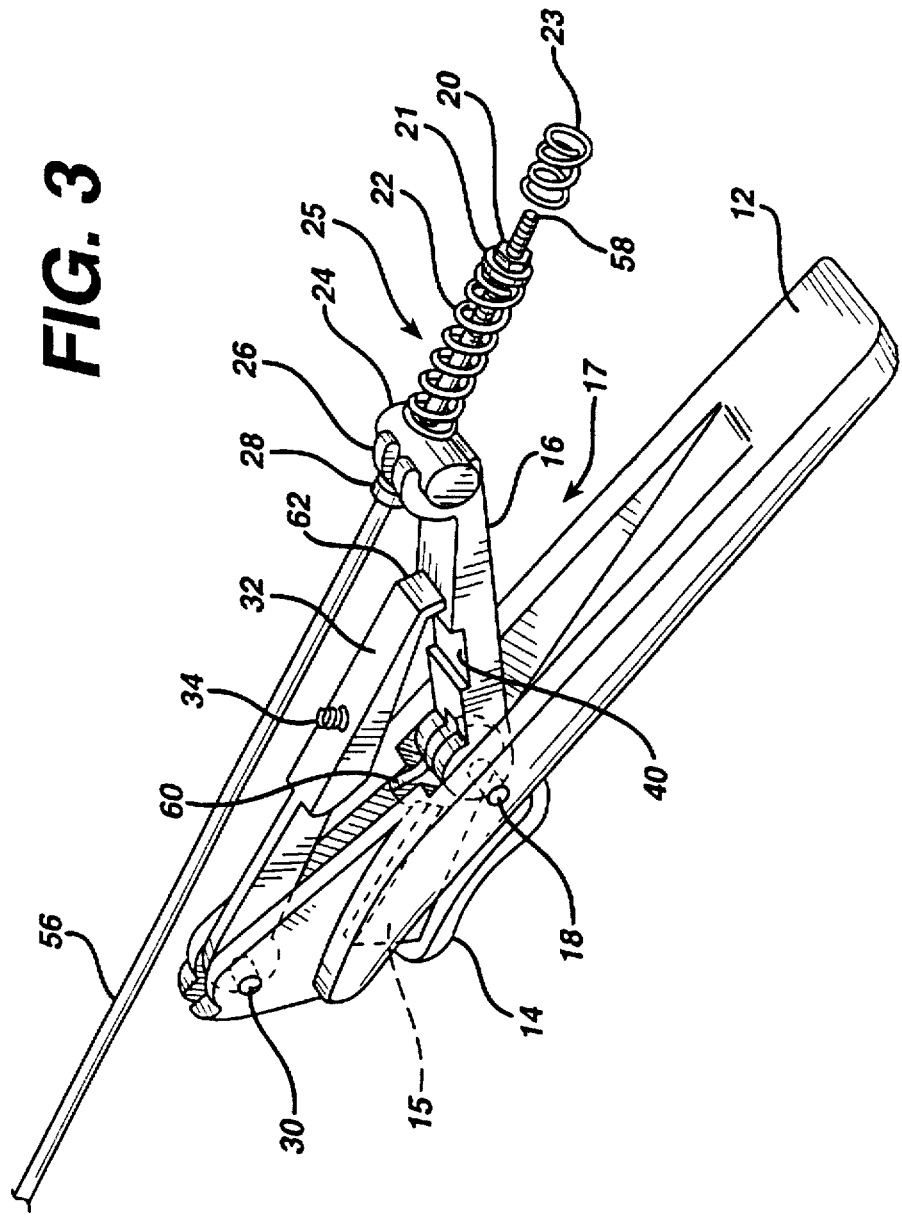
FIG. 3 is an isolated perspective view of the assembled handle latching mechanism with release trigger according to the present invention.
Figure 4:
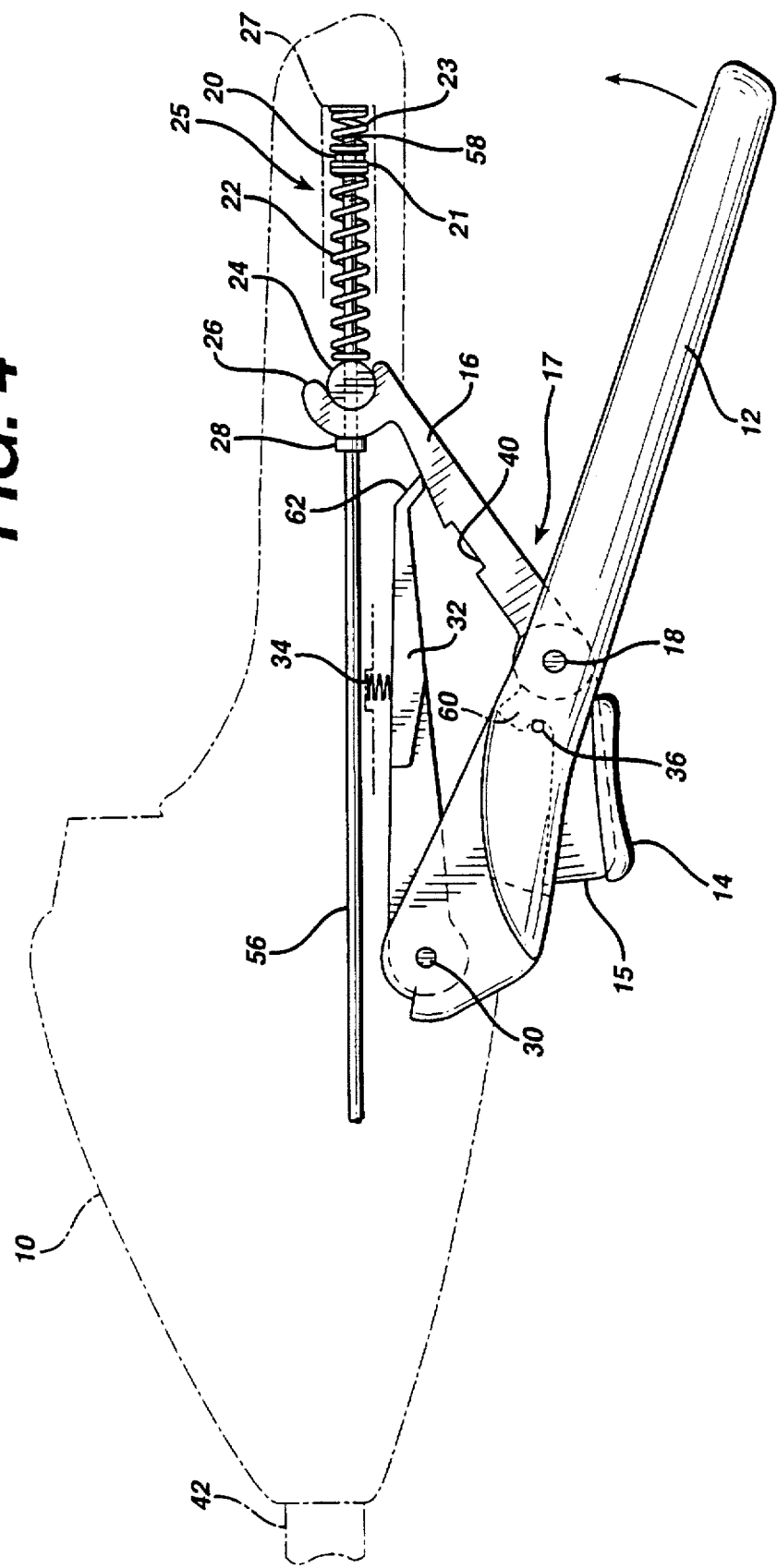
FIG. 4 is a side view of a handle latching mechanism according to the present invention shown in a first, unlatched open position.
Figure 5:
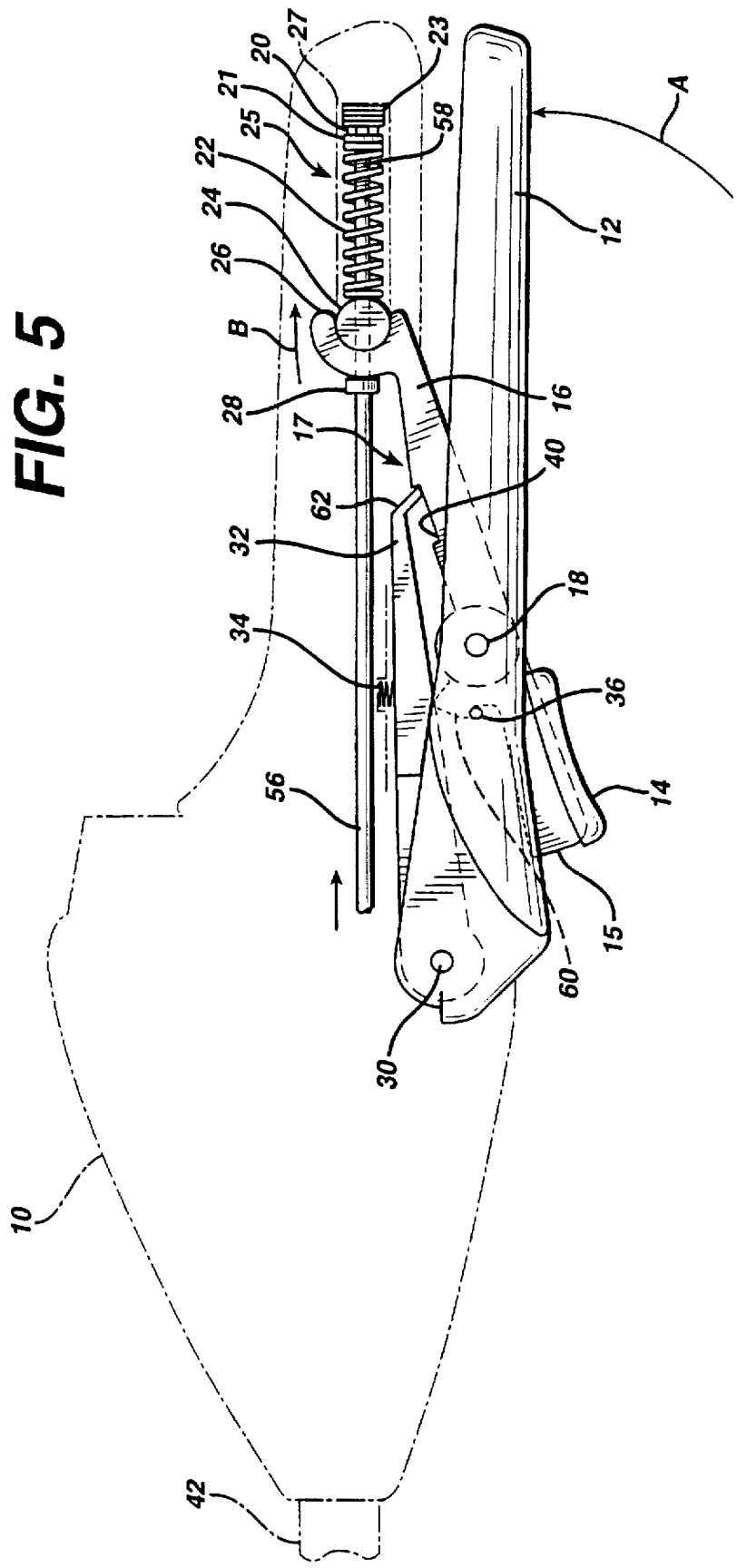
FIG. 5 is a side view of a handle latching mechanism according to the present invention shown in a second, latched closed position.

FIG. 3 is an isolated perspective view of the assembled handle latching mechanism with release trigger according to the present invention. In FIG. 3, latching mechanism 17 is in an open position. FIGS. 4–7 are side views of a handle latching mechanism according to the present invention showing the latching mechanism in operation. The instrument illustrated in FIG. 4 may be actuated by moving instrument trigger 12 toward instrument body 10. As illustrated in FIG. 5, the movement of instrument trigger 12 along path A is translated to toggle link 16 through pivot pin 18, forcing toggle link yoke 26 against yoke pin 24. Movement of yoke pin 24 is translated to compression spring 22 and through compression spring 22 to adjustment washer 21 and adjustment nut 20. Adjustment nut 20 being fixed to actuation rod 56, movement of adjustment nut 20 causes a proximal motion of the actuation rod 56 along path B. As illustrated in FIG. 1, proximal movement of actuation rod 56 actuates end effector linkages 50 and 52, closing end effector jaws 46 and 48. Since yoke pin 24 slides freely along actuation rod 56, when end effector jaws 46 and 48 engage tissue or other objects, further movement of instrument trigger 12 is absorbed by compression spring 22. Thus, the pressure applied by jaws 46 and 48 may be controlled by controlling the spring constant of compression spring 22. As instrument trigger 12 is compressed, latch tab 62 of latching link 32 slides along toggle link 16 until latch tab 62 engages latch notch 40. Compression spring 34 acts to force latch tab 62 against latch link 16 and into latch notch 40.

Figure 6:
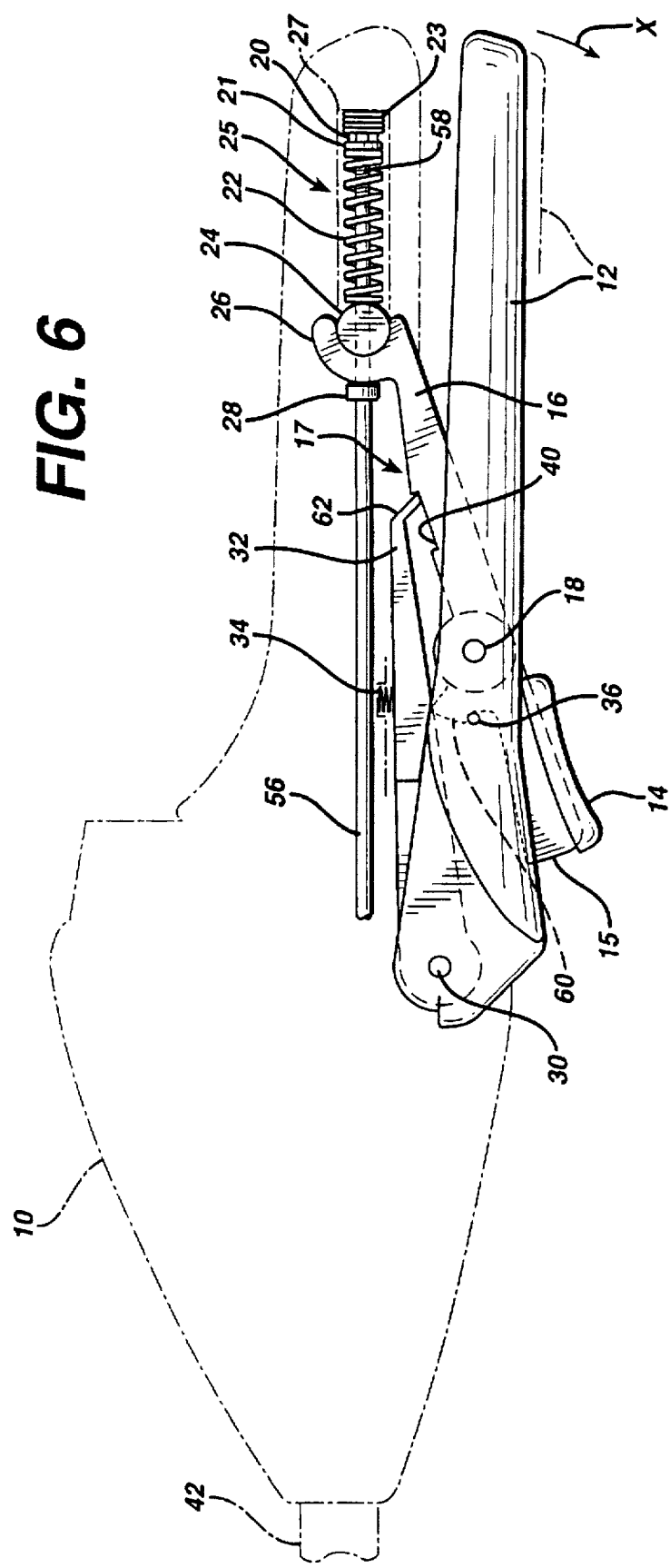
FIG. 6 is a side view of a handle latching mechanism according to the present invention in a third, ready to release position.

As illustrated in FIG. 6, once latch tab 62 has engaged latch notch 40, instrument trigger 12 remains locked even after it is released. Compression spring 22 and return spring 23 apply force to toggle link yoke 26, moving it in a distal direction and forcing instrument trigger 12 to move in direction X. However, movement of toggle link 16 is limited by latch link 32. When latch tab 62 reaches the proximal edge of latch notch 40 the latch mechanism locks in the closed position. While in this condition, instrument trigger 12 can be squeezed and released without releasing latching mechanism 17.

Figure 7:
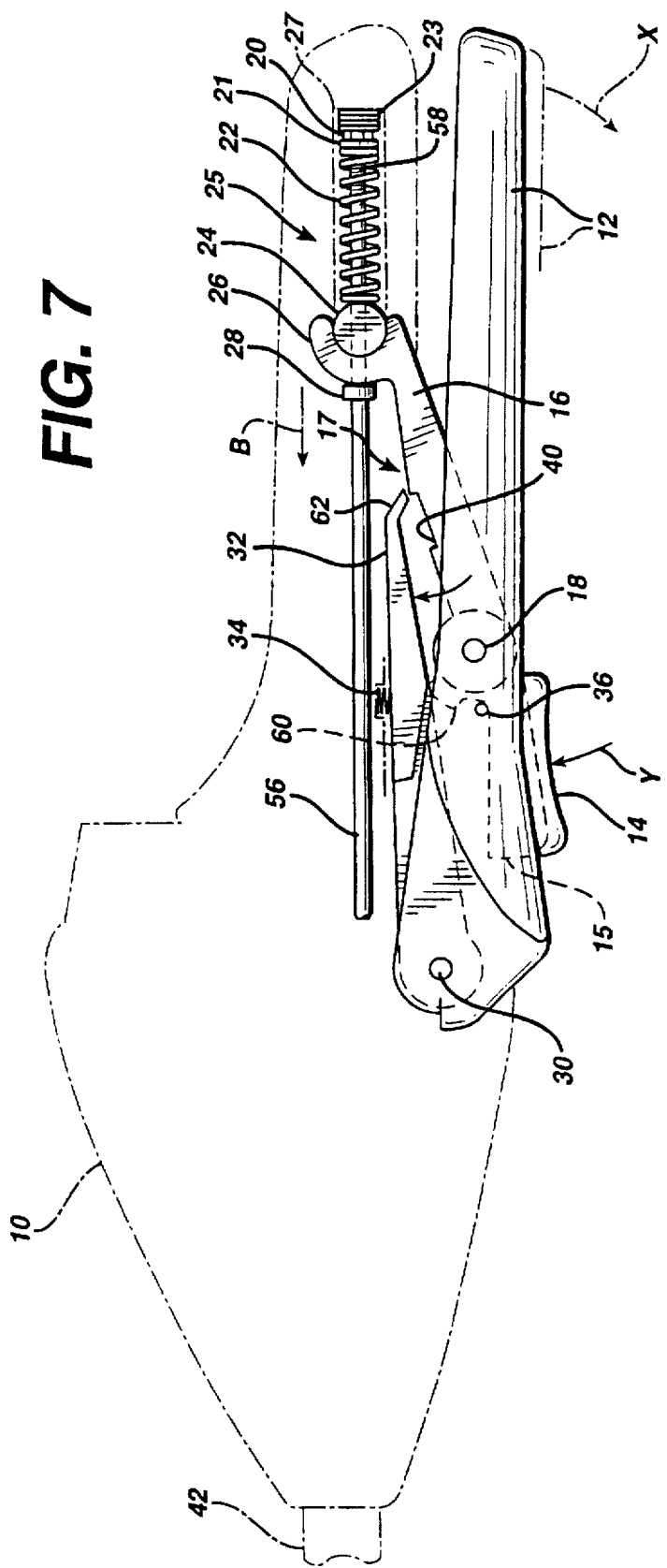
FIG. 7 is a side view of a handle latching mechanism according to the present invention in a fourth, disengaging position after pressing the release trigger.

As illustrated in FIG. 7, to release latching mechanism 17 and, thus, jaws 46 and 48 of end effector 44, instrument trigger 12 is squeezed to move latch tab 62 away from the proximal end of latch notch 40. Then release button 14 is depressed along path Y, moving trigger 15 and, thus, release tab 60 against latch link 32. This causes latch link 32 to lift out of latch notch 40, thereby releasing latching mechanism 17. As illustrated in FIG. 7, releasing trigger 12 causes compression spring 22 and return spring 23 to force yoke pin 24 along path B against actuation rod stop 28 opening end effector 44. The force from compression spring 22 and return spring 23 is also translated to instrument trigger 12 through toggle link yoke 26 and toggle link 16, forcing instrument trigger 12 open along path X as pressure is released by the operator.

Figure 8:
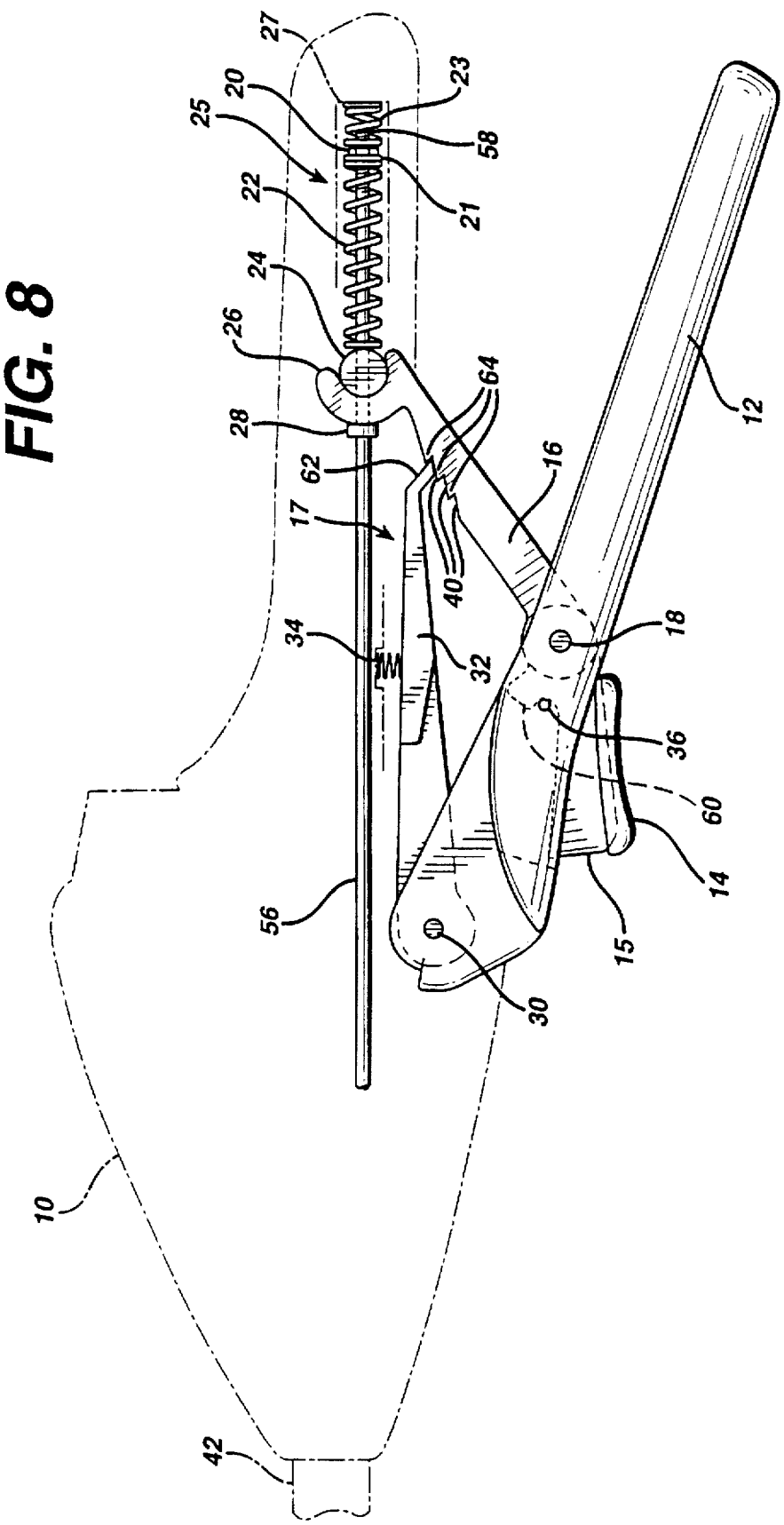
FIG. 8 is a side view of a further embodiment of a handle latching mechanism according to the present invention wherein the handle may be latched in a plurality of positions.

FIG. 8 is a side view of a further embodiment of a handle latching mechanism according to the present invention wherein the handle may be latched in a plurality of positions. In FIG. 8, a plurality of latch notches 40 are separated by a plurality of latch notch peaks 64. In the embodiment illustrated in FIG. 8, movement of instrument trigger 12 toward instrument body 10 forces latch tab 62 to slide along toggle link 16 over latch notch peaks 64 and into latch notches 40. Instrument trigger 12 is prevented from releasing by the slope of the distal side of latch notch peaks 64 which is angled to prevent latch tab 62 from slipping out of latch notch 40. The proximal side of latch notch peaks 64 are angled to facilitate movement of latch tab 62 along toggle link 16 as instrument trigger 12 is closed. Thus, in the embodiment illustrated in FIG. 8, instrument trigger 12 may be locked in a plurality of closed positions according to which of latch notches 40 latch tab 62 stops in. Once instrument trigger 12 has been latched in place, it may be closed further by forcing latch trigger 12 toward instrument body 10. Alternatively, in the embodiment illustrated in FIG. 8, instrument trigger 12 may be released from any of its locked positions by closing instrument trigger 12 slightly to move latch tab 62 away from the distal side of latch notchpeak 64 and forcing release trigger 15 against instrument trigger 12 which, in turn, forces release tab 60 against latch link 32, forcing latch tab 62 out of latch notch 40.

Figure 9:
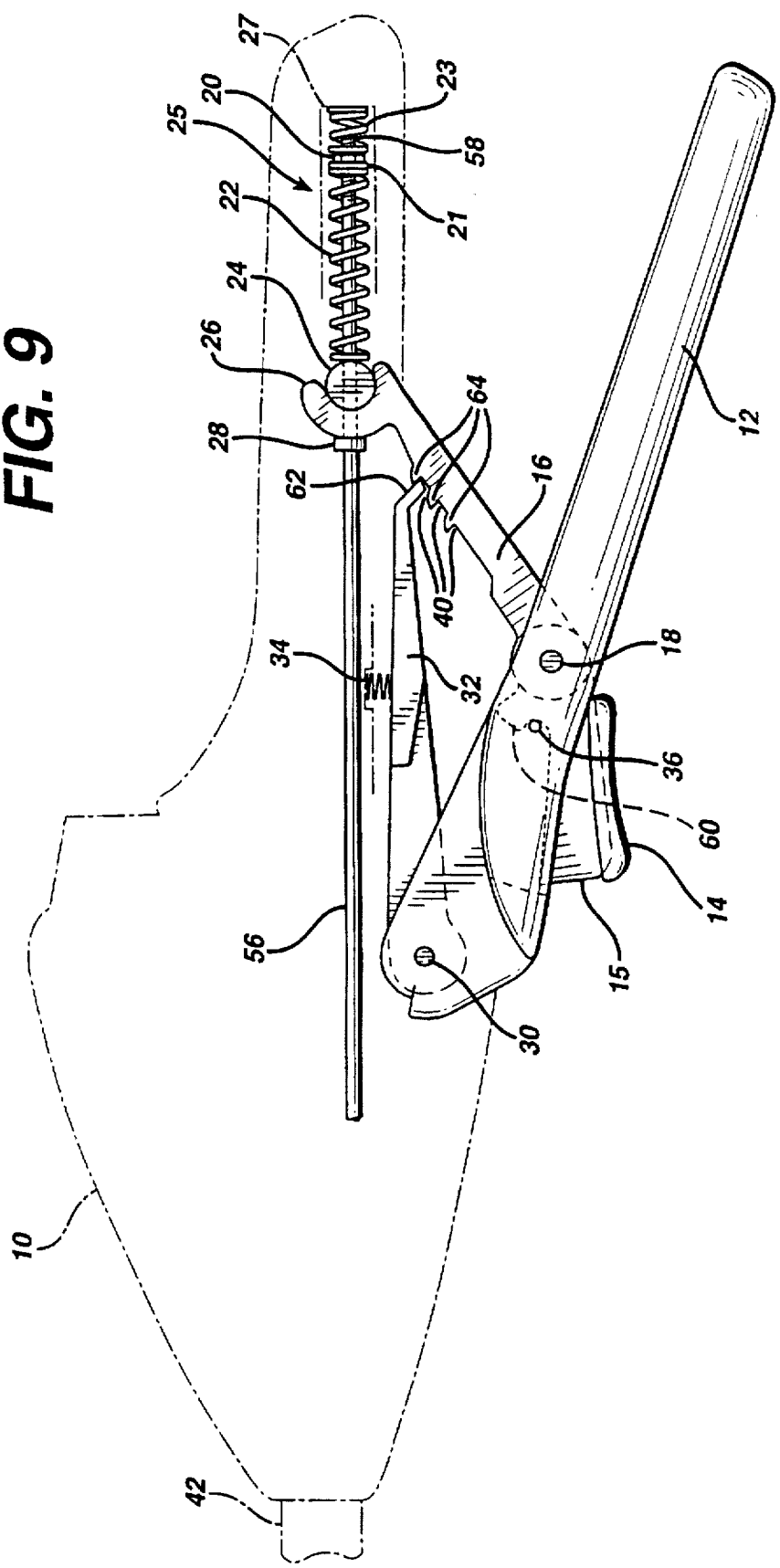
FIG. 9 is a side view of a further embodiment of a handle latching mechanism according to the present invention wherein the handle may be latched in a plurality of positions.

FIG. 9 is a side view of a further embodiment of a handle latching mechanism according to the present invention wherein the handle may be latched in a plurality of positions. In FIG. 9, a plurality of latch notches 40 are separated by a plurality of latch notch peaks 64. In FIG. 9, latch notch peaks 64 protrude from toggle link 16, forming latch notches 40 between latch notch peaks 64. In the embodiment illustrated in FIG. 9, movement of instrument trigger 12 toward instrument body 10 forces latch tab 62 to slide along toggle link 16 over latch notch peaks 64 and into latch notches 40. Instrument trigger 12 is prevented from releasing by the slope of the distal side of latch notch peaks 64 which is angled to prevent latch tab 62 from slipping out of latch notch 40. The proximal side of latch notch peaks 64 are rounded to facilitate movement of latch tab 62 along toggle link 62 as instrument trigger 12 is closed. Thus, in the embodiment illustrated in FIG. 9, instrument trigger 12 may be locked in a plurality of closed positions according to which of latch notches 40 latch tab 62 stops in. Once instrument trigger 12 has been latched in place, it may be closed further by forcing latch trigger 12 toward instrument body 10. Alternatively, in the embodiment illustrated in FIG. 9, instrument trigger 12 may be released from any of its locked positions by closing instrument trigger 12 slightly to move latch tab 62 away from the distal side of latch notchpeak 64 and forcing release trigger 15 against instrument trigger 12 which, in turn, forces release tab 60 against latch link 32, forcing latch tab 62 out of latch notch 40.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A latching mechanism for a surgical instrument, said latching mechanism comprising:

a toggle link connecting a first grip member to a second grip member;

at least one latch notch in said toggle link;

a latch link adapted to fit into said latch notch when said first grip member is moved toward said second grip member; and a release trigger adapted to force said latch link out of said latch notch when said trigger is pressed and said first grip member is moved toward said second grip member.

2. A latching mechanism according to claim 1 wherein said toggle link includes a plurality of latch notches.

3. A surgical instrument including a handle, said handle comprising:

an instrument trigger pivotally connected to an instrument body;

a toggle link connecting said instrument trigger to an actuating mechanism in said handle;

a latch notch in said toggle link;

a latch link pivotally connected to said handle at a first end and contacting said toggle link at a second end; and a latch trigger adapted to contact said latch link.

4. A surgical instrument according to claim 3 wherein:

said toggle link is pivotally connected to said instrument trigger at a first end of said toggle link;

said latch link includes a spring mechanism to force said second end of said latch notch against said latch link; and said latch trigger contacts said latch link such that motion of said latch trigger acts against said spring mechanism.

5. A surgical instrument according to claim 4 wherein:

said latch notch is located between said first end of said toggle link and said actuating mechanism;

said latch trigger is pivotally connected to said instrument trigger.

6. A surgical instrument according to claim 4 wherein said toggle link includes a plurality of latch notches.

7. A handle latching mechanism for a surgical instrument including first and second handle elements, said handle latching mechanism comprising, a toggle link pivotally connected to said first handle element at a first end and connected to an actuating mechanism in said second handle element at a second end, said toggle link including a latch notch;

a latch link pivotally connected to said surgical instrument at a first end and slidably connected to said latch link at a second end;

a release trigger pivotally connected to said first handle element at a first end, said second end being adapted to force said latch link away from said toggle link when said second end of said latch link is in said latch notch and said release trigger is pressed.

8. A handle latching mechanism according to claim 7 wherein said handle latching mechanism further comprises a spring positioned between said latch link and said second handle element.

9. A handle element according to claim 8 wherein said spring acts to force said second end of said latch link against said toggle link.

* * * * *